US012672843B2

(12) United States Patent
Babbs et al.

(10) Patent No.: US 12,672,843 B2
(45) Date of Patent: Jul. 7, 2026

(54) MULTIWAVELENGTH ULTRASOUND SYSTEM AND METHOD

(71) Applicant: Purdue Research Foundation, West Lafayette, IN (US)

(72) Inventors: Charles F. Babbs, West Lafayette, IN (US); Mary Lang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 207 days.

(21) Appl. No.: 18/216,676

(22) Filed: Jun. 30, 2023

(65) Prior Publication Data

US 2024/0000419 A1 Jan. 4, 2024

Related U.S. Application Data

(60) Provisional application No. 63/357,016, filed on Jun. 30, 2022.

(51) Int. Cl.
*A61B 8/08* (2006.01)
*A61B 8/00* (2006.01)

(52) U.S. Cl.
CPC ............ *A61B 8/085* (2013.01); *A61B 8/4477* (2013.01)

(58) Field of Classification Search
CPC ......... A61B 8/08; A61B 8/0891; A61B 8/481; A61B 8/48
See application file for complete search history.

(56) References Cited

U.S. PATENT DOCUMENTS

| | | |
|---|---|---|
| 8,714,014 B2 | 5/2014 | Kaduchak et al. |
| 2014/0261721 A1 | 9/2014 | Kaduchak et al. |

FOREIGN PATENT DOCUMENTS

EP 2240927 B1 7/2021

OTHER PUBLICATIONS

Christakou et al. "Ultrasonic three-dimensional on-chip cell culture for dynamic studies of tumor immune surveillance by natural killer cells", 2015, Royal Society of Chemistry, 15, 3222 (Year: 2015).*

(Continued)

*Primary Examiner* — Anne M Kozak
*Assistant Examiner* — Kaitlyn Eunji Kim
(74) *Attorney, Agent, or Firm* — Purdue Research Foundation

(57) ABSTRACT

The multiwavelength ultrasound system includes a first ultrasound device, a second ultrasound device, and a processor. The multiwavelength ultrasound system aggregates and visualizes biological cells. The first ultrasound device is configured to produce a first ultrasound wave having a frequency lower than around 300 kHz. The first ultrasound wave is also configured to aggregate the biological cells. The second ultrasound device is configured to produce a second ultrasound wave having a frequency greater than around 300 kHz. The second ultrasound wave is also configured to visualize the biological cells by determining a location and/or a position of the biological cells. The processor is configured to selectively actuate at least one of the first ultrasound device and the second ultrasound device. The processor is configured to detect at least one of a density and/or a concentration of the biological cells.

19 Claims, 12 Drawing Sheets

(56) References Cited

OTHER PUBLICATIONS

Savoia et al., "A Low Frequency Broadband Flextensional Ultrasonic Transducer Array", 2016, IEEE Transactions on Ultrasonics, Ferroelectrics, and frequency control, vol. 63, No. 1 (Year: 2016).*

Mercado et al., "Estimating Cell Concentration in Three-Dimensional Engineered Tissues Using High Frequency Quantitative Ultrasound", 2014, Annals of Biomedical Engineering, vol. 42, No. 6, p. 1292-1304 (Year: 2014).*

Vanherberghen et al., "Ultrasound-controlled cell aggregation in a multi-well chip", 2010, Royal Society of Chemistry, 10, 2727-2732 (Year: 2010).*

Piyasena, M. E. et al., Multinode acoustic focusing for parallel flow cytometry. Anal. Chem. Feb. 21, 2012; 84(4): 1831-1839.

Ward, M. D. et al., Fundamentals of Acoustic Cytometry. Current Protocols in Cytometry, 84, e36, Apr. 2018.

Goddard, G.R. et al., Analytical Performance of an Ultrasonic Particle Focusing Flow Cytometer, Anal. Chem. 2007, 79, 8740-8746.

* cited by examiner 0 sec 2 sec 4 sec 8 sec $\phi = 0.00$ $\phi = 0.33$ $\phi = 0.67$ $\phi = 1.00$

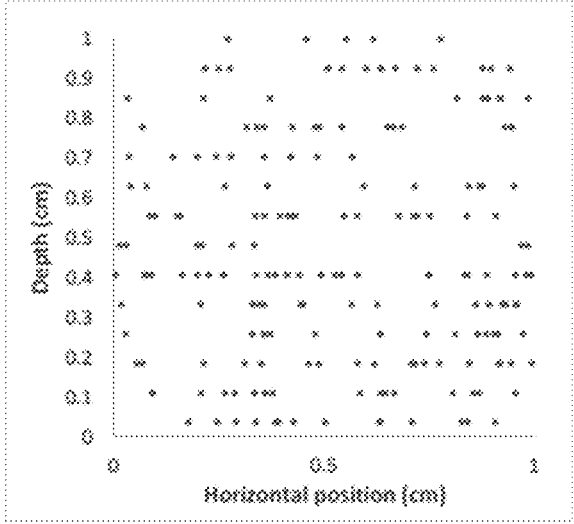
FIG. 5A
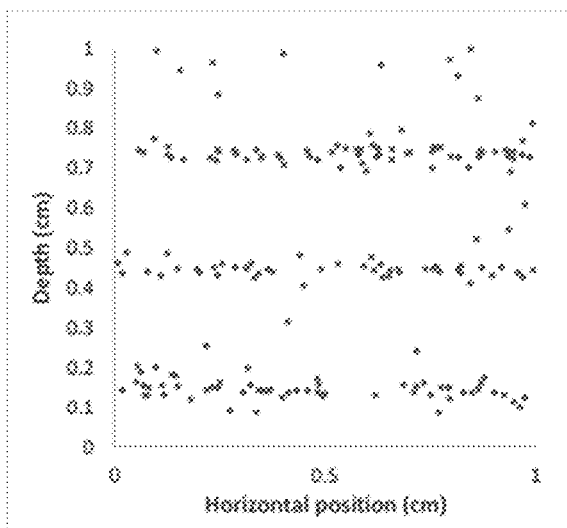
FIG. 5B
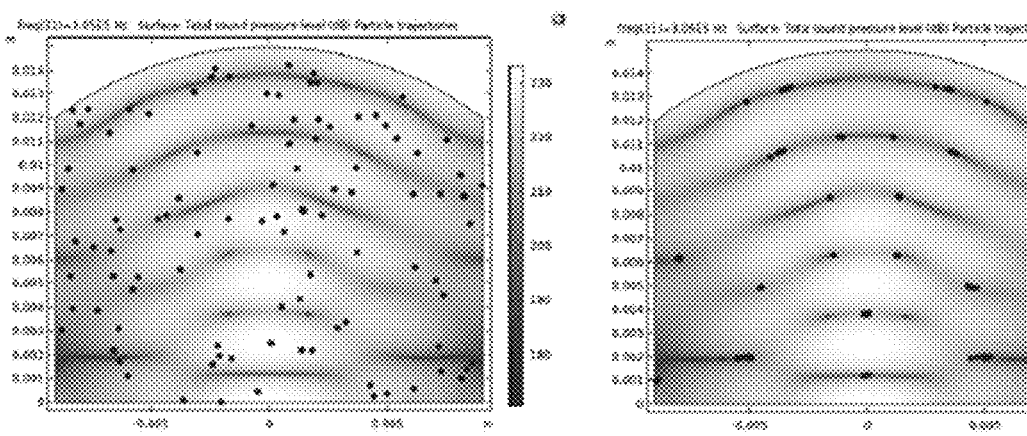
FIG. 6A                                    FIG. 6B

MULTIWAVELENGTH ULTRASOUND SYSTEM AND METHOD

CROSS REFERENCE TO RELATED APPLICATIONS

The present application is a U.S. non-provisional application which claims the benefit of U.S. provisional application Ser. No. 63/357,016, filed Jun. 30, 2022, the content of which is incorporated by reference herein in its entirety.

FIELD

The disclosure generally relates to ultrasound systems and, more particularly, to ultrasound systems for aggregating or focusing cells for subsequent visualization.

INTRODUCTION

This section provides background information related to the present disclosure which is not necessarily prior art.

Pediatricians are compelled with difficult decisions when an infant or young child comes into the emergency department with fever, fussiness, and poor feeding. Even though a simple viral infection is by far the most common cause, it is necessary to rule out bacterial meningitis. Bacterial meningitis may have severe downstream consequences, including permanent neurologic deficits, learning disabilities, and death. This situation currently requires a spinal tap or lumbar puncture to sample and examine the cerebrospinal fluid to determine if there are white blood cells present, indicating a bacterial or viral infection of the central nervous system, in contrast to an ordinary viral infection of the upper respiratory system. The lumbar puncture procedure causes significant stress and discomfort to both the child and the parents. Additionally, the lumbar puncture procedure imposes a significant cost burden. In the vast majority of cases the results are negative for bacterial meningitis. There is an unmet clinical need for a painless, noninvasive test for detection of abnormal cells in the cerebrospinal fluid, which is normally cell free.

Accordingly, there is a continuing need for a non-invasive detection system that is configured to visualize abnormal cells in the cerebrospinal fluid. Desirably, the non-invasive detection system may be configured to detect the abnormal cells more economically and more quickly than known methods such as a spinal tap or a lumbar puncture.

SUMMARY

In concordance with the instant disclosure, a multiwavelength ultrasound system that is configured to concentrate and then detect abnormal cells in the cerebrospinal fluid, has surprisingly been discovered. Desirably, the multiwavelength ultrasound system may more quickly first concentrate at longer wavelengths and then visualize at shorter wavelengths the abnormal cells in the cerebrospinal fluid for a fraction of the costs of known methods such as a spinal tap or a lumbar puncture.

The multiwavelength ultrasound system is configured to aggregate and determine a location and/or a position of acoustically focused biological cells in an aqueous media. In a specific example, the biological cells may include white blood cells. The multiwavelength ultrasound system may include a first ultrasound device, a second ultrasound device, and a processor. The first ultrasound device may be configured to produce a first ultrasound wave having a frequency lower than around 300 kHz. The first ultrasound wave may also be configured to aggregate the biological cells via acoustic focusing. The second ultrasound device may be configured to produce a second ultrasound wave having a frequency greater than around 300 kHz. The second ultrasound wave may also be configured to determine the location and/or the position the biological cells. The processor may be configured to selectively actuate the first ultrasound device(s) and/or the second ultrasound device. The processor may be configured to determine a density and/or a presence of the biological cells or contaminants such as bacteria. Additionally, the processor may be configured to output a concentration or confirmation of the presence or absence of the biological cells.

Various ways of using the multiwavelength ultrasound system configured to aggregate and determine a location and/or a position of acoustically focused biological cells are provided. For instance, a method may include a step of providing a first ultrasound device, a second ultrasound device, and a processor. The first ultrasound device may be configured to produce a first ultrasound wave having a frequency lower than around 300 kHz. The first ultrasound wave may also be configured to aggregate the biological cells, such as white blood cells, via acoustic focusing. The second ultrasound device may be configured to produce a second ultrasound wave having a frequency greater than around 300 kHz. The second ultrasound wave may be configured to determine the position and/or the presence of the acoustically focused biological cells or clumps of cells. The processor may be configured to selectively actuate at least one of the first ultrasound device and the second ultrasound device, determine a density of the biological cells, and/or output a concentration of the biological cells. Next, the first ultrasound system may generate the first ultrasound wave. The biological cells may then be aggregated. The second ultrasound system may generate the second ultrasound wave. Then, the location and/or the position of the biological cells may be determined. Afterwards, the density or presence of the biological cells may be identified. A concentration of the biological cells may also be determined.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 5A is a schematic diagram of particles aggregating into particularly narrow shaped bands when subjected to a plane wave ultrasound at a first frequency, according to one embodiment of the present disclosure;

FIG. 5B is a schematic diagram of particles aggregating into particularly broad shaped bands when subjected to a plane wave ultrasound at a second frequency, which is different from the first frequency as shown in FIG. 5A, according to one embodiment of the present disclosure;

FIG. 6A is a computer-generated simulation of particles disposed in a fluid, further depicting the particles dispersed throughout the fluid, according to one embodiment of the present disclosure;

FIG. 6B is a computer-generated simulation of the particles, as shown in FIG. 6A, further depicting the particles aggregating into particularly arc-shaped bands when subjected to a plane wave ultrasound having a frequency at around 300 kHz, according to one embodiment of the present disclosure;

Figure 9:
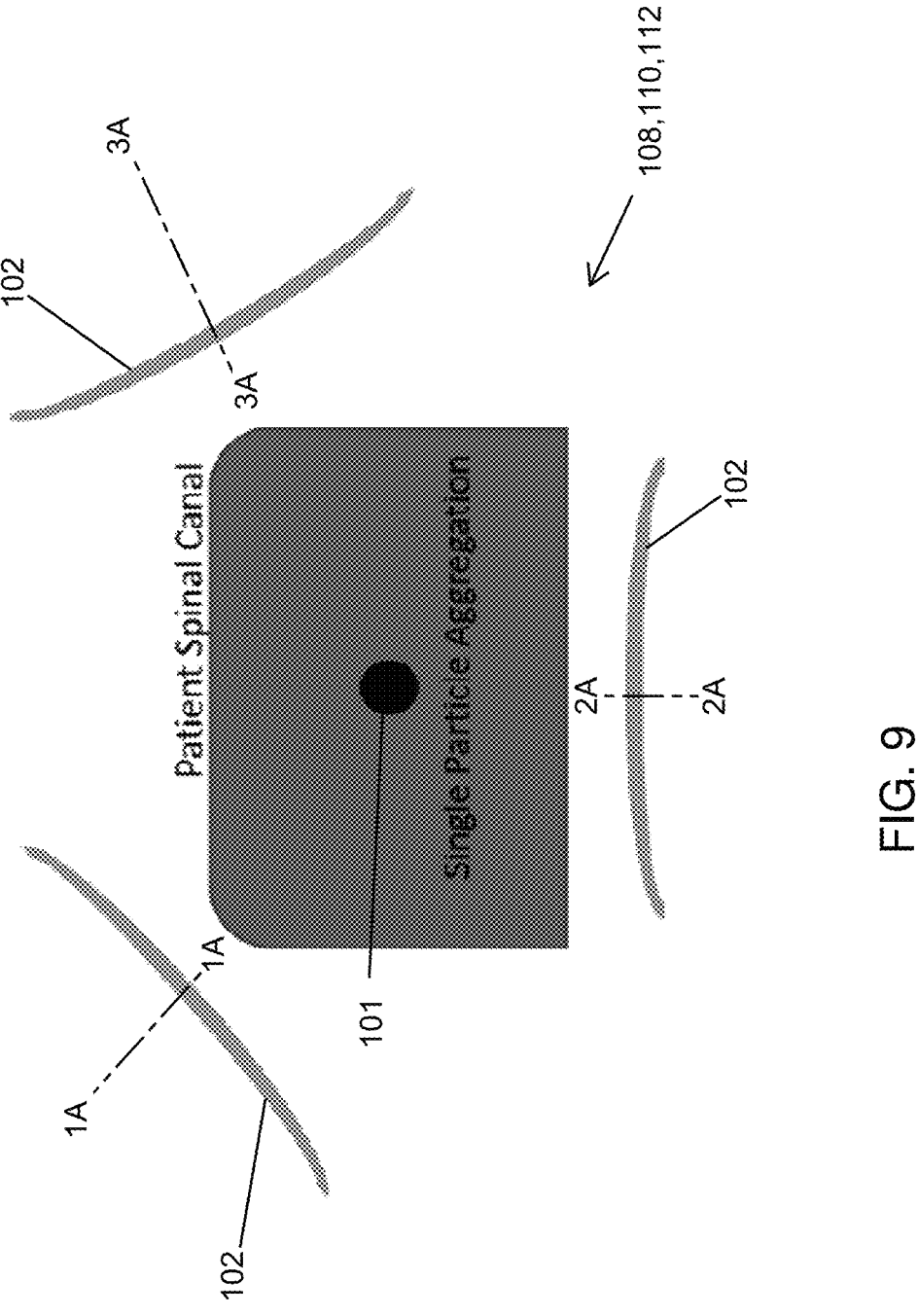
Figure 10:
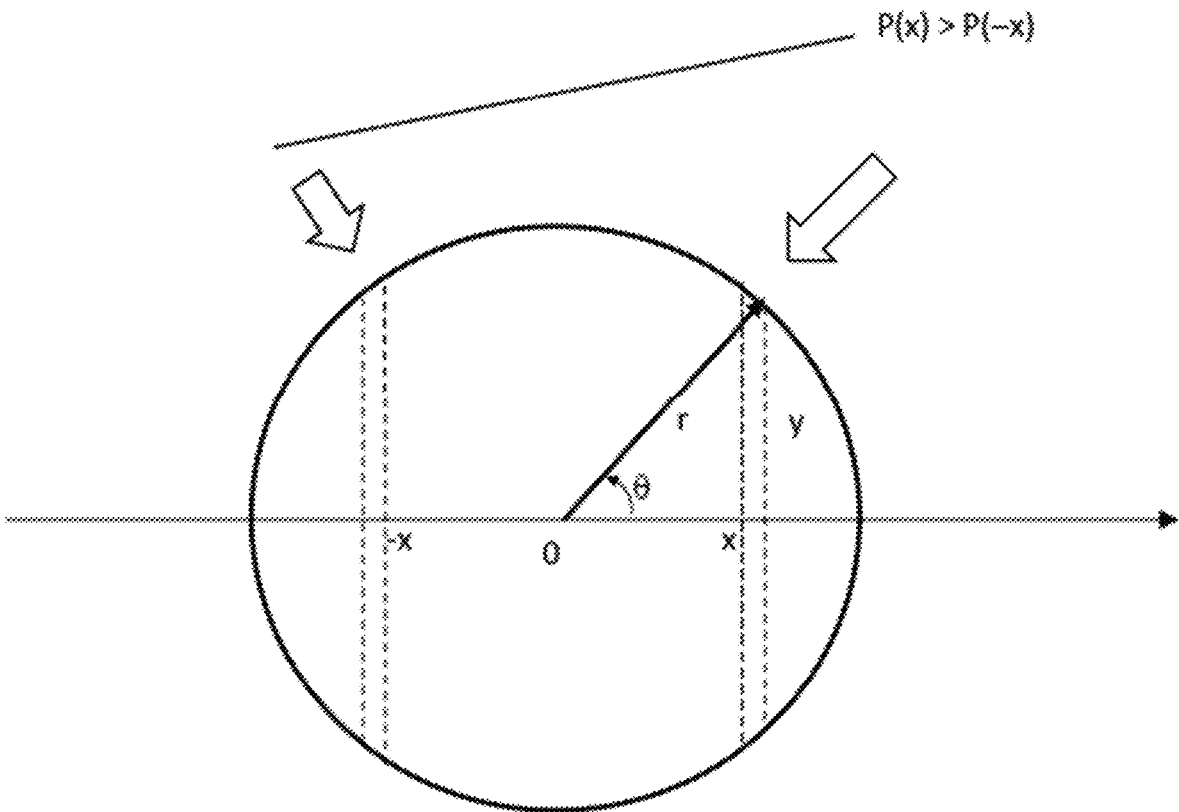
Figure 11:
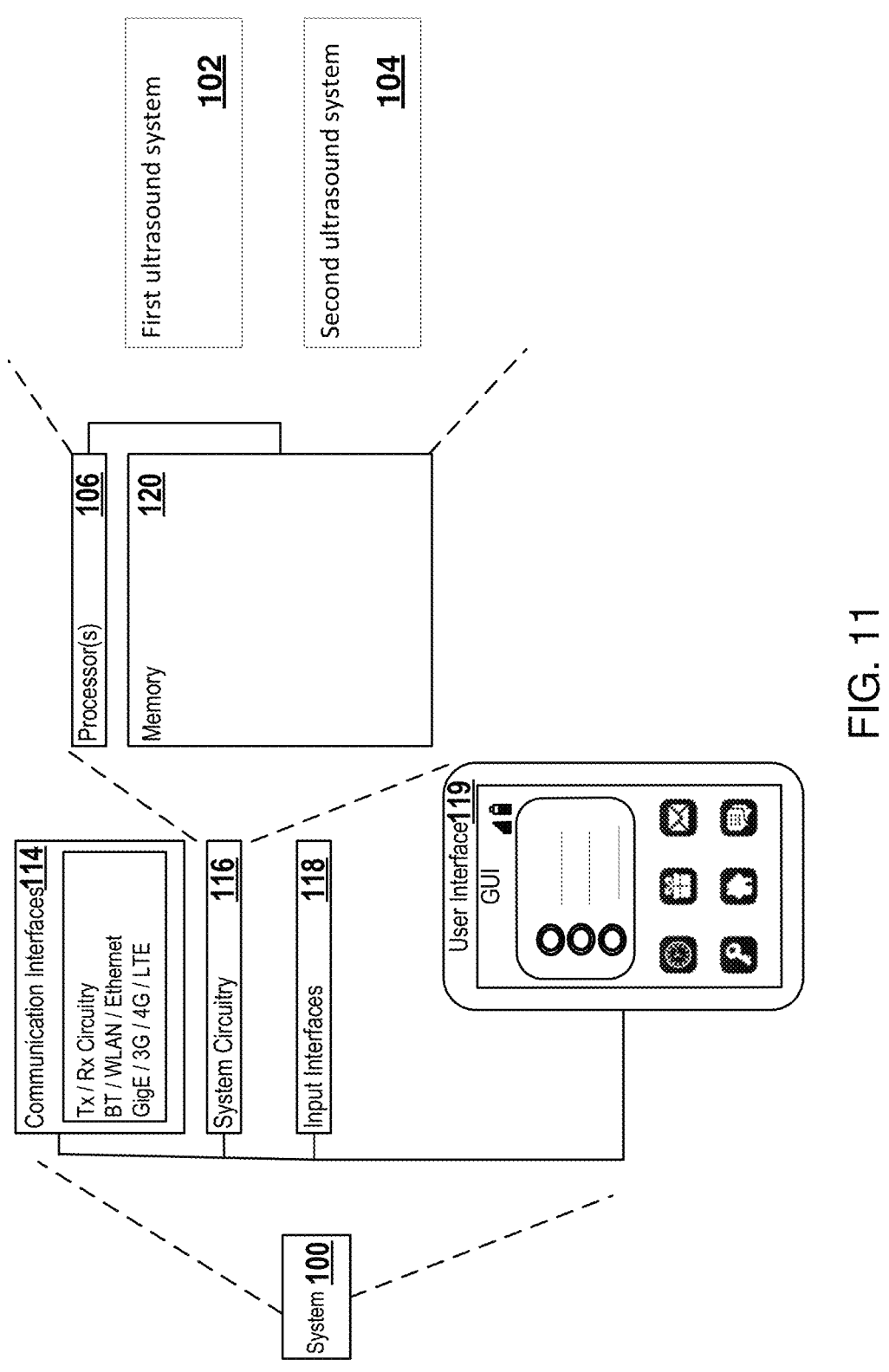
Figure 12:
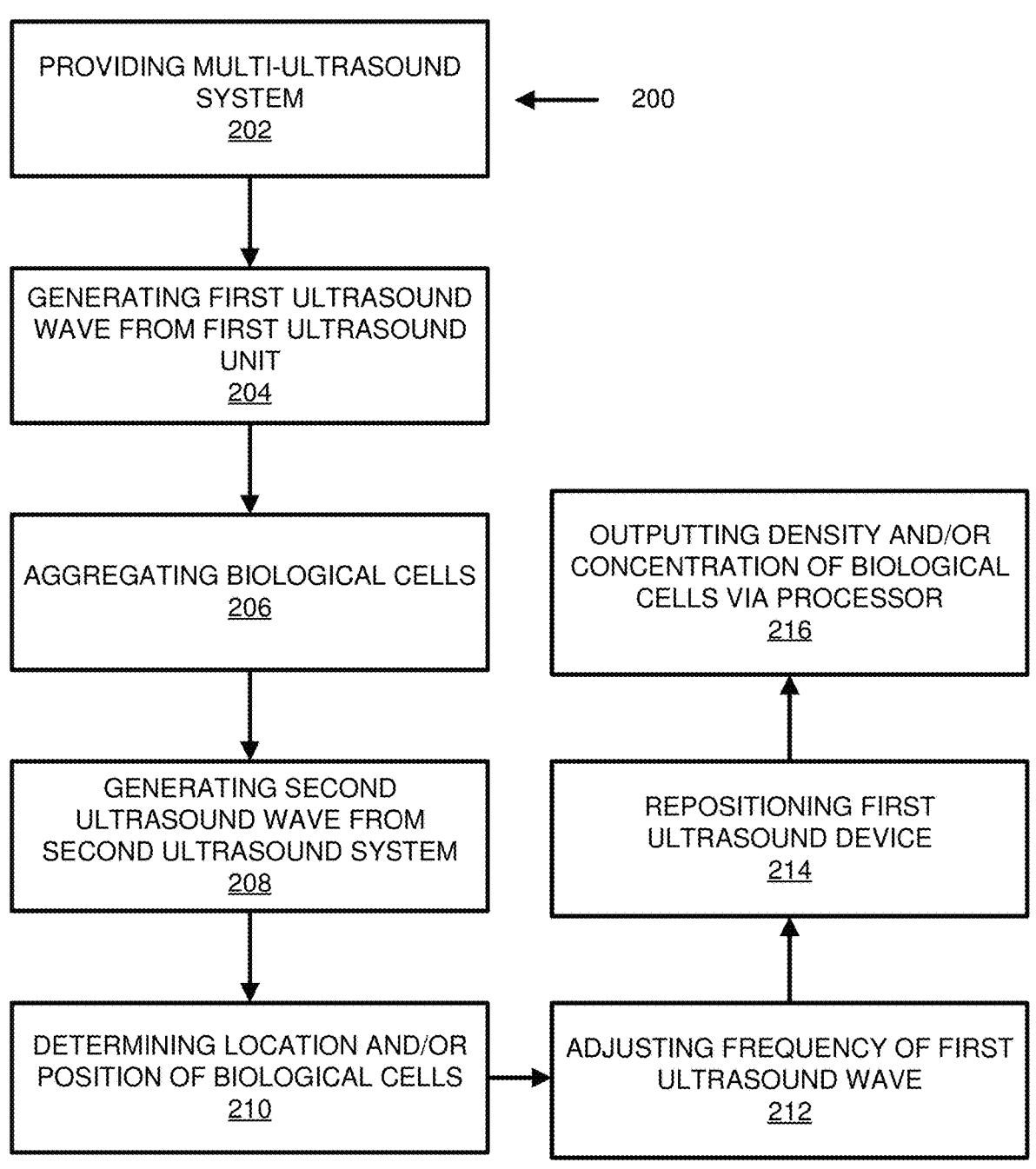

FIG. 9 is a top-plan view of a schematic diagram of particles being aggregated into a cluster based on utilizing a plurality of first ultrasound devices disposed on a first position, a second position, and a third position, further depicting each of the plurality of first ultrasound devices being simultaneously engaged while substantially equally positioned along a circumference of the area being examined, according to one embodiment of the present disclosure;

FIG. 10 is a schematic view of an idealized spherical particle in a pressure gradient along an x-dimension, further depicting the pressure pushes perpendicular to the surface of the spherical particle at all levels, according to one embodiment of the present disclosure;

FIG. 11 is a schematic diagram of the multiwavelength ultrasound system, further depicting the system having a communication interface, an input interface, a user interface, and a system circuitry, wherein the system circuitry may include a processor and a memory, according to one embodiment of the present disclosure; and FIG. 12 is a flowchart depicting a method for using the multiwavelength ultrasound system, according to one embodiment of the present disclosure.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the FIG. is turned over, elements described as "below," or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present disclosure may utilize acoustic standing waves to move particles suspended in a fluid-filled cavity, by means of a time-averaged drift force that pushes them toward nodal planes of pressure. This is the basis for ultrasonic cell sorting. There are gradual changes in slopes of the standing pressure waves with increasing distance from each node. With every little push of the particle toward the node, it will reach a position where the restoring force pushing it back toward the antinode is slightly less than the original force that drove it away from the antinode. This process over many cycles results in creep of the particle away from the antinode toward the node. In planar standing waves, particles typically become regularly spaced at half-wavelength intervals perpendicular to the direction of sound propagation. The present disclosure includes a fast and efficient computational approach to simulate and/or determine the movement of particles to nodal locations within a standing wave field. One specific approach may work for idealized plane waves in one dimension with variable reflection, frequency, particle size, fluid density, fluid viscosity, and standing wave pressure.

Figure 1:
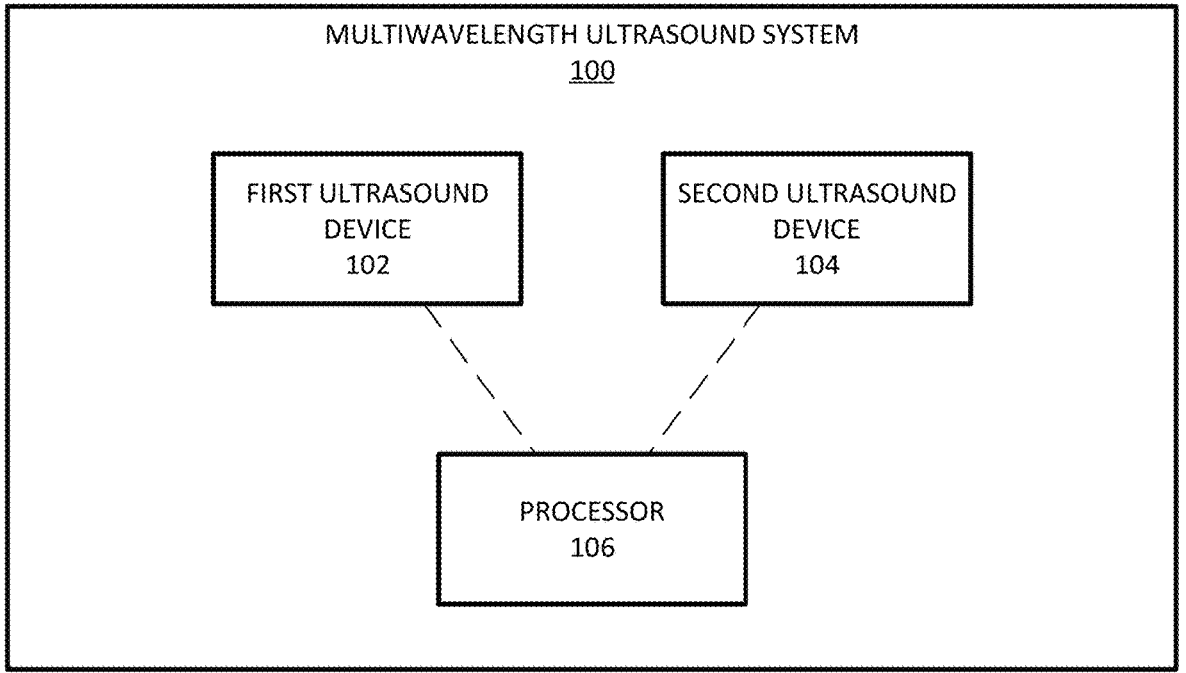
FIG. 1 is a box diagram of the components of a multiwavelength ultrasound system, according to one embodiment of the present disclosure.

The multiwavelength ultrasound system 100 is configured to aggregate and determine a location and/or a position of acoustically focused biological cells 101 in an aqueous media. In a specific example, the biological cells 101 may include white blood cells. As shown in FIG. 1, the multiwavelength ultrasound system 100 may include a first ultrasound device 102, a second ultrasound device 104, and a processor 106. The first ultrasound device 102 and the second ultrasound device 104 may be communicatively coupled to the processor. The first ultrasound device 102 may be configured to produce a first ultrasound wave having a frequency lower than around 300 kHz. In a specific example, the first ultrasound device 102 may be configured to produce the first ultrasound wave having a frequency around 105 kHz. The first ultrasound wave may also be configured to aggregate the white blood cells. The second ultrasound device 104 may be configured to produce a second ultrasound wave having a frequency greater than around 300 kHz. In a more specific example, the second ultrasound wave may have a frequency greater than around 1 MHz. The second ultrasound wave may be configured to visualize the biological cells 101. It should be appreciated that visualization may include a representative display of the biological cells 101 for a user to visually observe. The term "visualize" may also be understood as the capacity for the ultrasound to resolve the biological cells 101 from the aqueous media and for the processor 106 to determine the positioning and/or the location of the biological cells 101. In a specific example, the processor 106 may include a display for visualizing the biological cells 101. The processor 106 may be configured to selectively actuate at least one of the first ultrasound device 102 and the second ultrasound device 104. Additionally, the processor 106 may be configured to output a concentration of biological cells 101. For instance, the processor 106 may output a concentration of the biological cells 101 and compare the concentration of the biological cells 101 to a predetermined threshold. In a specific example, the multiwavelength ultrasound system 100 may be capable of detecting a concentration with a minimum threshold of around three to thirty cells per cubic millimeter. As a non-limiting example, the predetermined threshold may be between around ten to around one-hundred cells per microliter before concentration as an indicator of bacterial meningitis. Advantageously, the multiwavelength ultrasound system 100 may autonomously determine if the concentration obtained from the processor 106 exceeds the predetermined threshold. In a non-limiting example, the multiwavelength ultrasound system 100 may be used in a white blood cell ultrasonography device.

Figure 2:
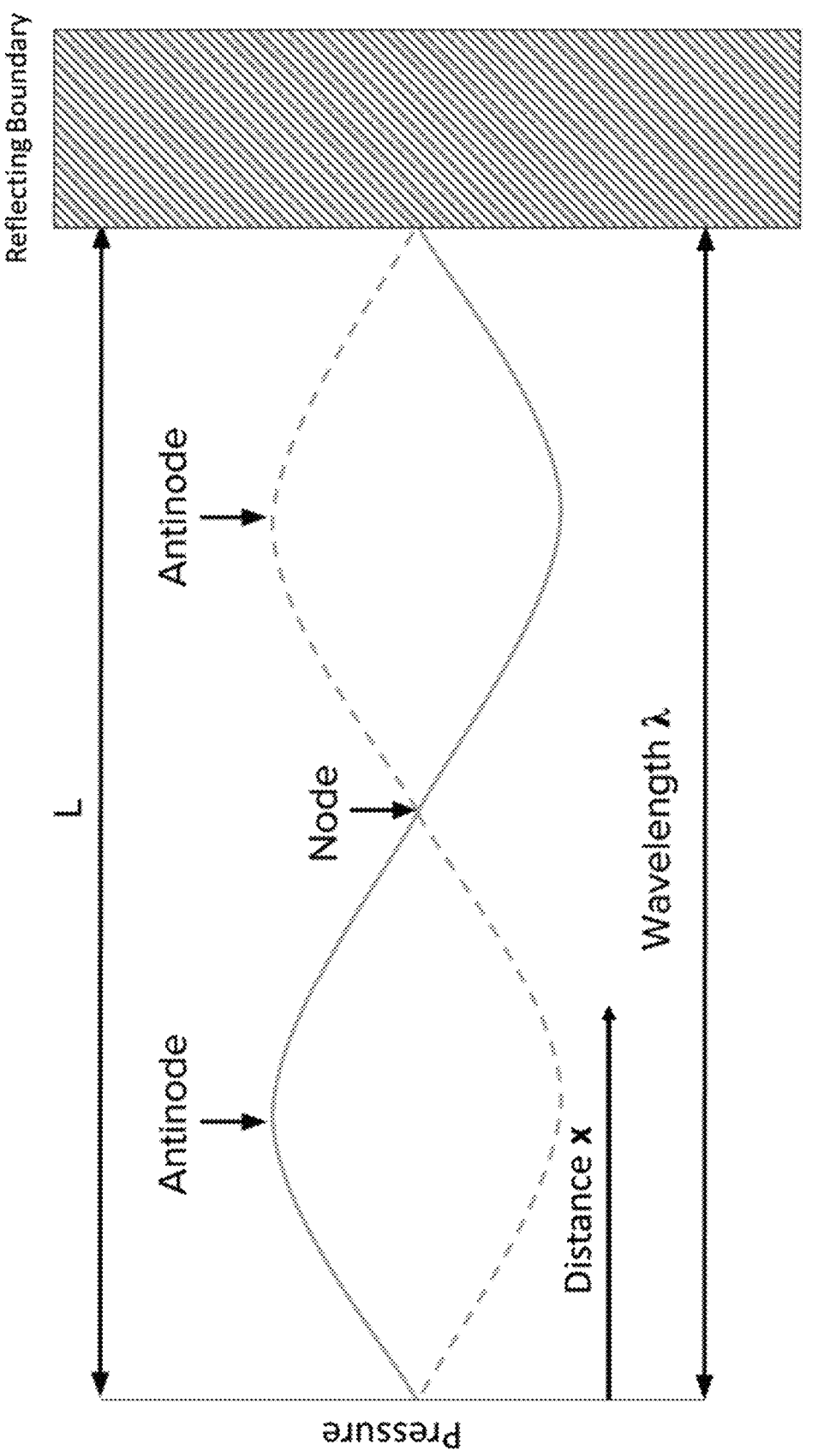
FIG. 2 is a model space illustrating a reflected plane wave, further depicting the incident and the reflected waves exactly cancelling at the nodes and reinforce at the antinodes, according to one embodiment of the present disclosure.
Figure 3A:
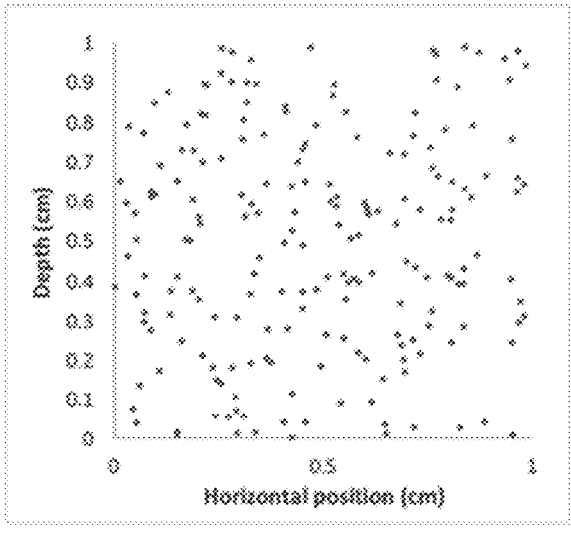
FIG. 3A is a schematic diagram of particles disposed in a fluid, further depicting the particles dispersed throughout the fluid, according to one embodiment of the present disclosure.
Figure 3B:
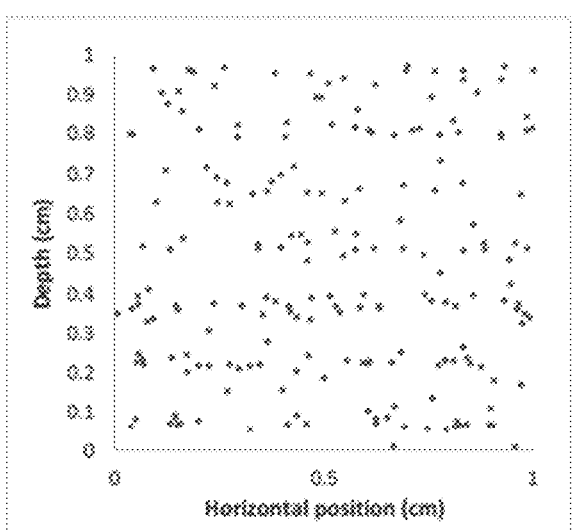
FIG. 3B is a schematic diagram of particles disposed in the fluid, as shown in FIG. 3A, further depicting the particles aggregating over time when subjected to a plane wave ultrasound, according to one embodiment of the present disclosure.
Figure 3C:
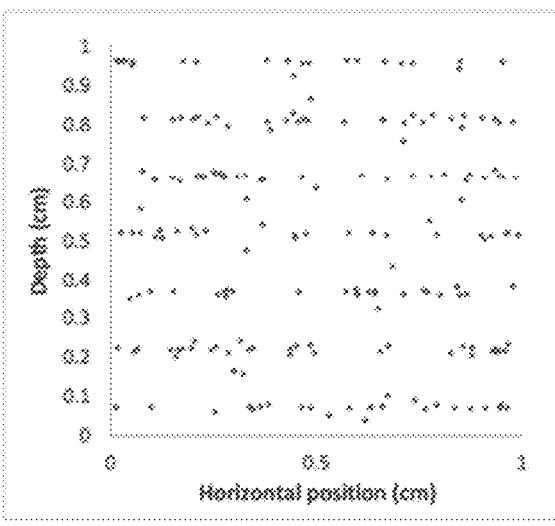
FIG. 3C is a schematic diagram of particles disposed in the fluid, as shown in FIGS. 3A-3B, further depicting the particles continuing to aggregate over time when subjected to a plane wave ultrasound, according to one embodiment of the present disclosure.
Figure 3D:
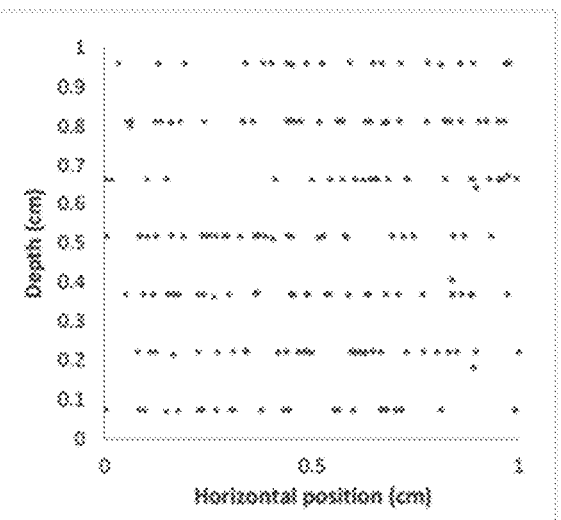
FIG. 3D is a schematic diagram of particles disposed in the fluid, as shown in FIGS. 3A-3C, further depicting the particles aggregating into substantially parallel lines over time when subjected to a plane wave ultrasound, according to one embodiment of the present disclosure.
Figure 4A:
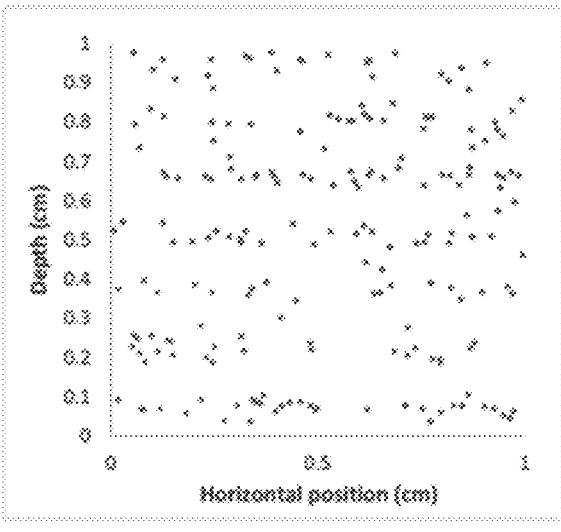
FIG. 4A is a schematic diagram of particles disposed in a fluid, further depicting the particles dispersed throughout the fluid, according to one embodiment of the present disclosure.
Figure 4B:
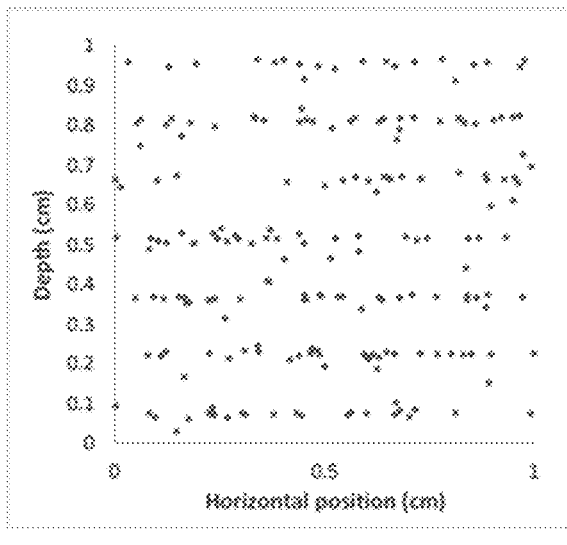
FIG. 4B is a schematic diagram of particles disposed in the fluid, as shown in FIG. 4A, further depicting the particles aggregating when subjected to a plane wave ultrasound with a reflection coefficient of 0.33, according to one embodiment of the present disclosure.
Figure 4C:
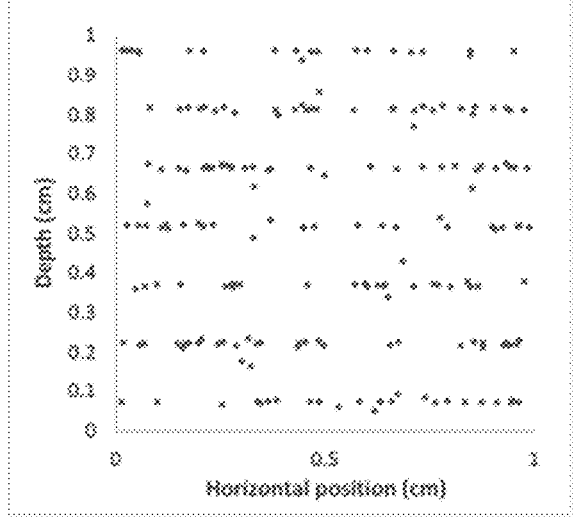
FIG. 4C is a schematic diagram of particles disposed in the fluid, as shown in FIGS. 4A-4B, further depicting the particles continuing to aggregate further when subjected to a plane wave ultrasound with a reflection coefficient of 0.67, according to one embodiment of the present disclosure.
Figure 4D:
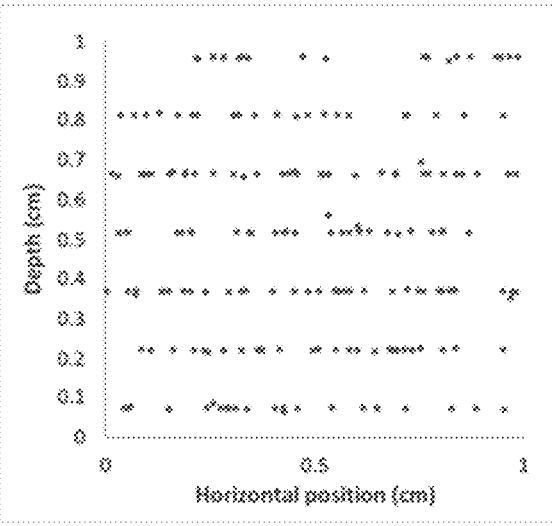
FIG. 4D is a schematic diagram of particles disposed in the fluid, as shown in FIGS. 4A-4C, further depicting the particles continuing to aggregate further when subjected to a plane wave ultrasound with a reflection coefficient of 1.00, according to one embodiment of the present disclosure.
Figure 7A:
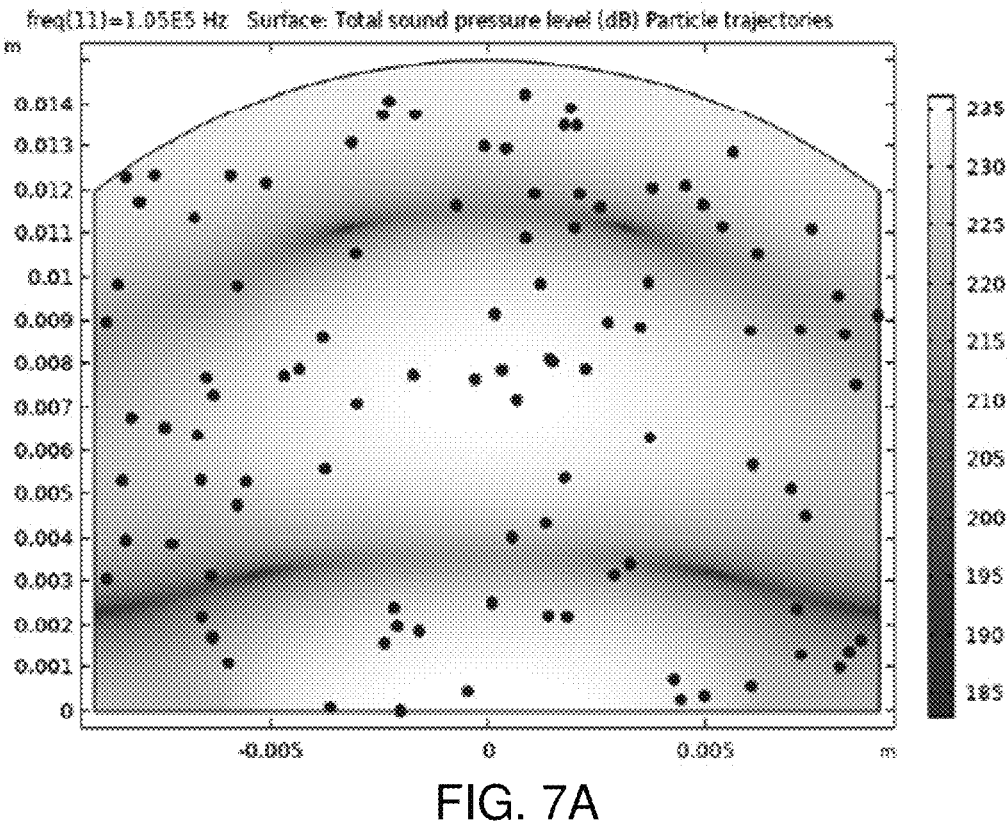
FIG. 7A is a computer-generated simulation of particles disposed in a fluid, further depicting the particles dispersed throughout the fluid, according to one embodiment of the present disclosure.
Figure 7B:
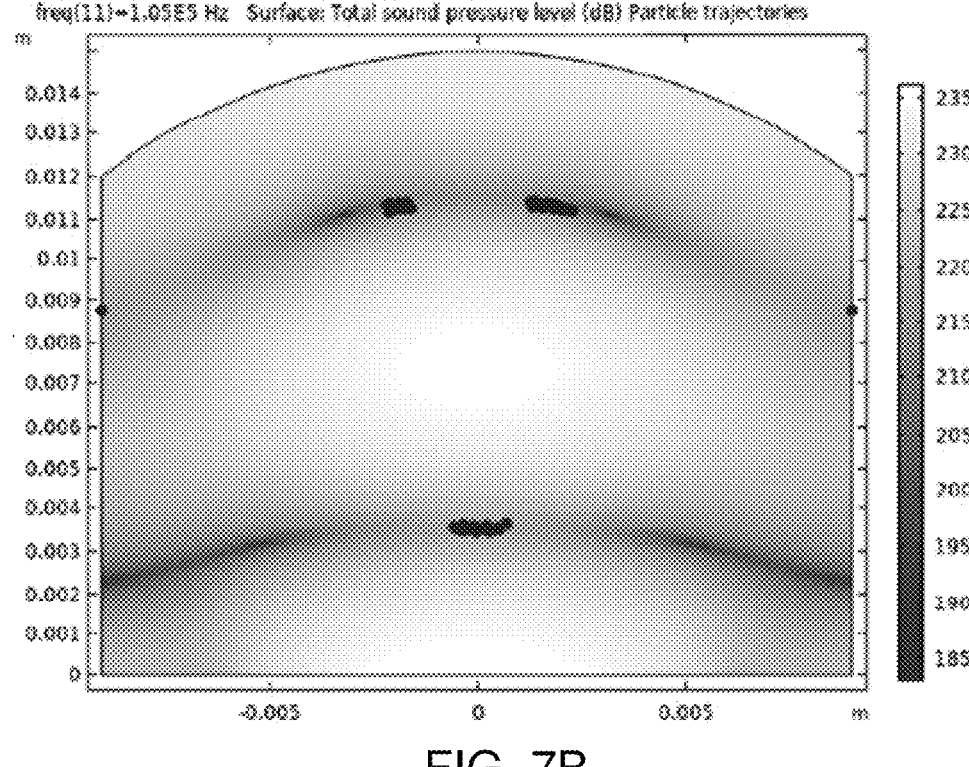
FIG. 7B is a computer-generated simulation of particles, as shown in FIG. 7A, further depicting the particles aggregating into clusters when subjected to a plane wave ultrasound having a frequency at around 105 kHz, according to one embodiment of the present disclosure.

The first ultrasound device 102 may include various ways to aggregate particles and biological cells 101, such as white blood cells. FIG. 2 illustrates features of a standing wave created by the summation of forward and reflected waves. As further shown in FIG. 2, the movement of the particles in a standing wave of acoustic pressure includes gradually migrating toward nodal planes of pressure. Without being bound to any particular theory it is believed that there are gradual changes in slopes of the standing pressure waves with increasing distance from each antinode. With every little push of the particle toward the node, it will reach a position where the restoring force pushing it back toward the antinode is slightly less than the original force that drove it away from the antinode. This process over many cycles may result in creep of the particle away from the antinode toward the node. If such creep of the particle is a significant result of the underlying physics, then scattered white blood cells suspended in cerebrospinal fluid or in urine may clump together at the nodes, making a bigger target that is much easier to detect with ultrasound than individual cells. Such clumping behavior is here shown to occur also in partial standing waves created by incomplete reflection and to a lesser degree in pure moving waves. It is contemplated that the utility of partial standing waves and/or pure moving waves may expand the applicability of the present disclosure. In a specific example, the present disclosure may be utilized to provide idealized plane waves in one dimension with variable reflection, frequency, particle size, fluid density, fluid viscosity, and standing wave pressure. With continued reference to FIG. 2, the pressure source is on the left and the reflecting boundary is on the right. Solid and dashed curves show the extreme limits of the algebraic sum of incident and reflected waves. With complete reflection, the combined incident and reflected waves exactly cancel at the nodes and reinforce at the antinodes.

In certain circumstances, as shown in FIGS. 3A-6D, the particles and/or cells may be aggregated in various ways. It should be understood that aggregation refers to the formation or grouping into a cluster. In a specific example, the particles and/or cells may be grouped into substantially parallel lines. In another specific example, the particles and/or cells may be grouped into substantially arc-shaped lines. In a more specific example, the spacing between the aggregated lines of particles and/or cells may be adjusted by varying a frequency of the first ultrasound wave. Desirably, the first ultrasound wave may be adjusted to a desired frequency that enhances the visibility of the particles and/or cells. For instance, the particles and/or cells may be more visible where the particles and/or cells are aggregated into fewer lines with greater spacing between each of the lines, as shown in FIG. 5B. One skilled in the art may select other suitable shapes to aggregate the particles and/or cells into, within the scope of the present disclosure.

In certain circumstances, the positioning of the first ultrasound device 102 and the second ultrasound device 104 may be configured to enhance the aggregation and visualization of the particles and/or cells. In a specific example, the first ultrasound device 102 may be disposed in a substantially perpendicular position from the second ultrasound device 104. For instance, as shown in FIG. 10, where the particle and/or cell is substantially spherical, the pressure of the first ultrasound wave may push substantially perpendicular to the particle and/or cell from any orientation in relation to the second ultrasound wave. One skilled in the art may select a particular orientation and/or positioning of the first ultrasound device 102 and the second ultrasound device 104 to enhance the aggregation and visualization of the particles and/or cells, within the scope of the present disclosure.

It is also contemplated that the first ultrasound wave and the second ultrasound wave may be provided by the first ultrasound device 102 alone, i.e., without the need of the second ultrasound device 104. In a specific example, the first ultrasound wave may have a frequency less than around 300 kHz. In a more specific example, the first ultrasound wave may have a frequency around 105 kHz. The first ultrasound wave may be configured to aggregate the white blood cells. The second ultrasound wave may have a frequency greater than around 300 kHz. In a more specific example, the second ultrasound wave may have a frequency greater than around 1 MHz.

Various ways of using the multiwavelength ultrasound system 100 configured to aggregate and visualize biological cells 101, such as white blood cells, are provided. For instance, as shown in FIG. 12, a method 200 may include a step 202 of providing a first ultrasound device 102, a second ultrasound device 104, and a processor 106. The first ultrasound device 102 may be configured to produce a first ultrasound wave having a frequency lower than around 300 kHz. The first ultrasound wave may also be configured to aggregate the biological cells 101. The second ultrasound device 104 may be configured to produce a second ultrasound wave having a frequency greater than around 300 kHz. The second ultrasound wave may also be configured to visualize the biological cells 101. The processor 106 may be configured to selectively actuate at least one of the first ultrasound device 102 and the second ultrasound device 104, detect at least one of the location and the density of the biological cells 101, and/or output a concentration of the biological cells 101. Next, the multiwavelength ultrasound system 100 may generate the first ultrasound wave. The biological cells 101 may then be aggregated utilizing acoustic focusing. The second ultrasound wave may be generated. Then, the biological cells 101 may be visualized. Afterwards, the location and/or the density of the biological cells 101 may be identified. A concentration of the biological cells 101 may also be determined.

Figure 8A:
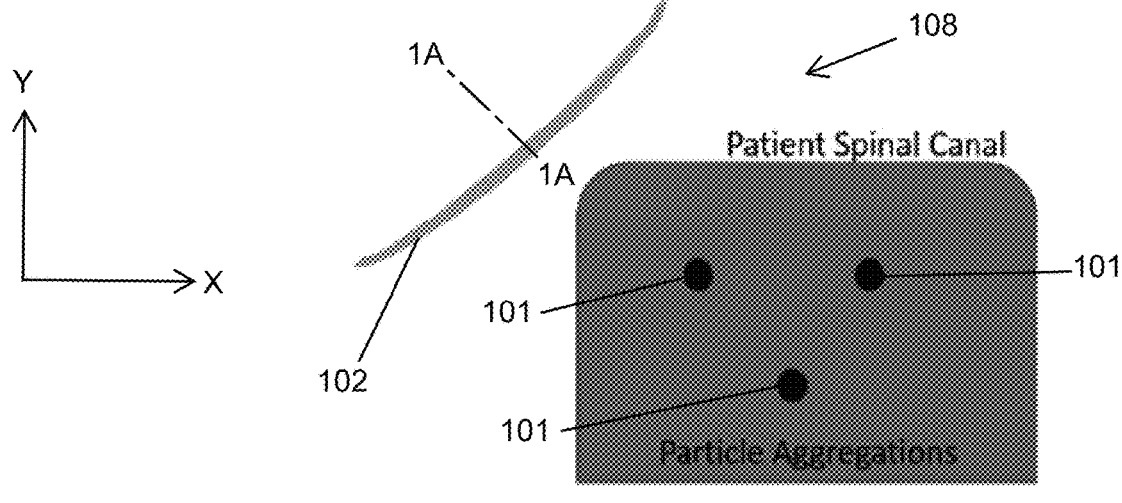
FIG. 8A is a top-plan view of a schematic diagram of particles disposed throughout the fluid in a spinal canal, further depicting a first ultrasound device being disposed in a first position along a first axis and applying a first ultrasound wave to aggregate the particles, according to one embodiment of the present disclosure.
Figure 8B:
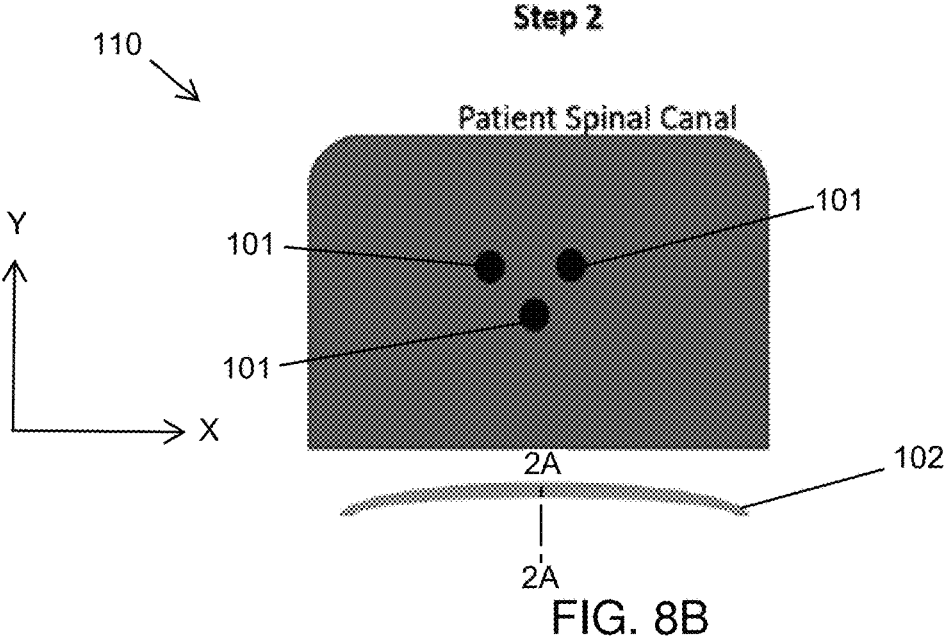
FIG. 8B is a top-plan view of the schematic diagram of particles, as shown in FIG. 8A, further depicting the first ultrasound device being disposed in a second position along a second axis and applying a first ultrasound wave to continue to aggregate the particles, according to one embodiment of the present disclosure.

In a specific example, the method 200 may further include the first ultrasound device 102 being disposed in a first position 108 along a first axis 1A, as shown in FIG. 8A. The first ultrasound device 102 may be utilized to aggregate particles along the first axis 1A. Then, the first ultrasound device 102 may be repositioned in a second position 110 along a second axis 2A, as shown in FIG. 8B. The second axis 2A may be substantially transverse to the first axis 1A.

US 12,672,843 B2

9

10

Figure 8C:
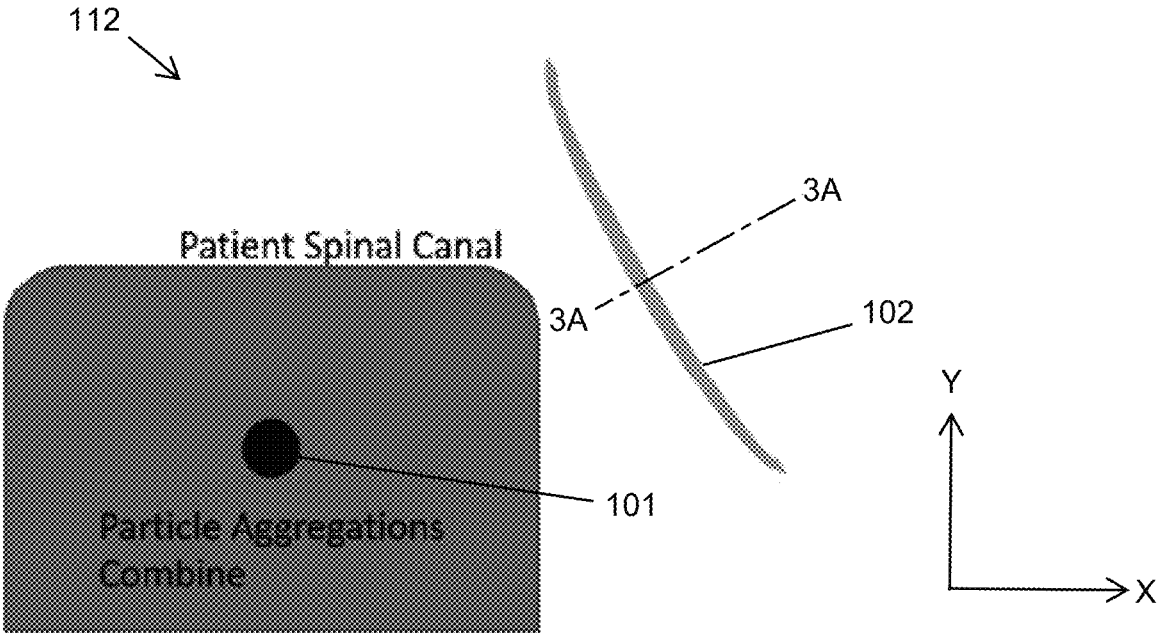
FIG. 8C is a top-plan view of a schematic diagram of particles, as shown in FIGS. 8A-8B, further depicting the first ultrasound device being disposed in a third position along a third axis and applying a first ultrasound wave to continue to aggregate the particles, according to one embodiment of the present disclosure.

More specifically, the second position 110 may be rotated around a circumference of the area being examined, such as a spinal cord of a patient. The first ultrasound device 102 may be then utilized to aggregate the particles along the second axis 2A. In a specific example, the first axis 1A may be substantially transverse to the second axis 2A. In a more specific example, the first ultrasound device 102 may be further repositioned in a third position 112 along a third axis 3A, as shown in FIG. 8C. The first axis 1A may be spaced at a substantially equilateral angle between each of the second axis 2A and/or the third axis 3A. More specifically, the third position 112 may be further rotated around the circumference of the area being examined. The first ultrasound device 102 may be then utilized to aggregate the particles along the third axis 3A. Thus, the particles may be aggregated into a cluster by aggregating the particles along each of the first axis 1A, the second axis 2A, and/or the third axis 3A. Advantageously, the particles aggregated into a cluster may be more easily identified by the second ultrasound device 104 to determine the location and/or the position of the particles/biological cells 101. In a more specific example, the processor 106 may be configured to autonomously reposition the first ultrasound device 102 between each of the first position 108, the second position 110, and/or the third position 112. One skilled in the art may select any number of positions and angles to aggregate the particles, within the scope of the present disclosure.

In certain circumstances, the first ultrasound device 102 may include a plurality of ultrasound devices disposed around a circumference of the area being examined, as shown in FIG. 9. More particularly, as a non-limiting example, the plurality of first ultrasound devices 102 may be each positioned at the first position 108, the second position 110, and/or the third position 112 simultaneously. Each of the plurality of first ultrasound devices 102 may be engaged substantially simultaneously to aggregate the particles into a cluster. It should be appreciated that a skilled artisan may select any number of first ultrasound devices 102 or any angle along the circumference of the area being examined to aggregate the particles into a cluster, within the scope of the present disclosure.

The multiwavelength ultrasound system 100 may utilize various means to aggregate and visualize the biological cells 101. Table 1 is provided below as a non-limiting example to explain certain characteristics the processor 106 may account for when aggregating and visualizing the biological cells 101:

TABLE 1

| Symbol | Definition | Units (cgs) |
|---|---|---|
| α, β | Arbitrary angles in trigonometric identities | radians |
| r | Spherical particle radius | cm |
| A | Particle cross section, $\pi r^2$ | cm² |
| $V_2$ | Spherical particle volume, $(4/3)\pi r^3$ | cm³ |
| P(x, t) | Sinusoidal sound pressure | dynes/cm² |
| $P_{max}$ | Maximum positive amplitude of sound pressure | dynes/cm² |
| b | Viscous drag coefficient | dynes/(cm/sec) |
| ρ | Density of surrounding fluid | g/cm³ |
| v | Particle velocity | cm/sec |
| x | Location of particle in x-dimension | cm |
| Δx | Change in location of particle in x-dimension | cm |
| $v_{creep}$ | Particle creep (drift) velocity over many cycles | cm/sec |
| t | Time | sec |
| dt | Time step for numerical integration | sec |
| f | Wave frequency | Hz |
| ω = 2πf | Angular wave frequency | Hz |
| k | Wave number | 1/cm |
| c | Wave speed | cm/sec |

TABLE 1-continued

| Symbol | Definition | Units (cgs) |
|---|---|---|
| η | Viscosity of surrounding fluid | g/cm/sec |
| φ | Reflection amplitude ratio | |

In certain circumstances, the processor 106 may include various ways to determine the location and/or the position of acoustically focused biological cells 101 in an aqueous media. For instance, the processor 106 may determine for creep velocity of the biological cell as a function of position, x. More specifically, the processor 106 may determine for creep velocity of the biological cell as a function of position, x, utilizing a first algorithm:

$$v_{creep} \approx \frac{1}{5}\frac{\pi}{f\lambda}\left(P_{max}\frac{r^2}{\eta\lambda}\right)^2 (1+\phi)^2 \sin(4\pi x/\lambda)$$

Alternatively, the first algorithm may be rearranged when noting that frequency×wavelength=sound speed, fλ=c, in terms of dimensionless creep velocity, $$\frac{v_{creep}}{c},$$

dimensionless pressure, $$\left(\frac{P_{max}}{f\eta}\right),$$

and dimensionless radius, $$\left(\frac{r}{\lambda}\right).$$

For instance, the processor 106 may determine for creep velocity of the biological cell as a function of position, x, utilizing a second algorithm:

$$\frac{v_{creep}}{c} \approx \frac{1}{5}\pi\left(\left(\frac{P_{max}}{f\eta}\right)\left(\frac{r}{\lambda}\right)^2\right)^2 (1+\phi)^2 \sin\left(4\pi\left(\frac{x}{\lambda}\right)\right)$$

Using the second algorithm, it is evident that the creep velocity depends strongly on the ratio of pressure to frequency and very strongly on the ratio of particle size to wavelength. Creep may be four times faster for complete standing waves with φ=1 than for waves without reflection (φ=0). However, even without reflection, particles will creep, as happens in acoustic levitation by single beam trapping.

To speed numerical computation of particle motion, it is contemplated that $\Delta x_1+\Delta x_2$ on each sound cycle is quite small compared to position, x, so that $v_{creep}$ is stable over several cycles. Hence, the processor 106 may further use classical numerical techniques, such as the Euler method, to integrate creep velocity over time in order to determine the total displacement of a particle from any chosen starting position, x. For reference, the Euler method is provided below, where F represents the derivative of y with respect to x, and h represents a fixed small increment in x:

$$Y_n = Y_{n-1} + hF(x_{n-1}, y_{n-1})$$

The time step for numerical integration of creep velocity can be longer than the period of the sound wave, namely 1/f. This may allow the processor 106 to quickly calculate movements of a population of particles in space and time for any chosen set of model parameters. One skilled in the art may use other suitable methods and algorithms to determine the location and/or the position of acoustically focused biological cells 101 in an aqueous media, within the scope of the present disclosure.

As shown in FIG. 11, the multiwavelength ultrasound system 100 may further include a communication interface 114, a system circuitry 116, and/or an input interface 118. The system circuitry 116 may include the processor 106 or multiple processors. The processor 106 or multiple processors execute the steps to selectively actuate the first ultrasound device 102 and/or the second ultrasound device 104, determine a density of the biological cells 101, and output a concentration of the biological cells 101. Alternatively, or in addition, the system circuitry 116 may include memory 120.

The processor 106 may be in communication with the memory 120. In some examples, the processor 106 may also be in communication with additional elements, such as the communication interfaces 114, the input interfaces 118, and/or the user interface 119. Examples of the processor 106 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 106 may be one or more devices operable to execute logic. The logic may include computer executable instructions or computer code stored in the memory 120 or in other memory that when executed by the processor 106, cause the processor 106 to perform the operations of a data collection system, such as a UAV-based photogrammetry, terrestrial laser scanning, and/or aerial LiDAR platform. The computer code may include instructions executable with the processor 106.

The memory 120 may be any device for storing and retrieving data or any combination thereof. The memory 120 may include non-volatile and/or volatile memory, such as a random-access memory (RAM), a read-only memory (ROM), an erasable programmable read-only memory (EPROM), or flash memory. Alternatively or in addition, the memory 120 may include an optical, magnetic (hard-drive), solid-state drive or any other form of data storage device. The memory 120 may be included in any component or sub-component of the system 100 described herein.

The user interface 119 may include any interface for displaying graphical information. The system circuitry 116 and/or the communications interface(s) 112 may communicate signals or commands to the user interface 119 that cause the user interface to display graphical information. Alternatively or in addition, the user interface 119 may be remote to the system 100 and the system circuitry 116 and/or communication interface(s) 104 may communicate instructions, such as HTML, to the user interface to cause the user interface to display, compile, and/or render information content. In some examples, the content displayed by the user interface 119 may be interactive or responsive to user input. For example, the user interface 119 may communicate signals, messages, and/or information back to the communications interface 104 or system circuitry 116.

The system 100 may be implemented in many different ways. In some examples, the system 100 may be implemented with one or more logical components. For example, the logical components of the system 100 may be hardware or a combination of hardware and software. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 120, for example, that comprises instructions executable with the processor 106 or other processor to implement one or more of the features of the logical components. When any one of the logical components includes the portion of the memory that comprises instructions executable with the processor 106, the component may or may not include the processor 106. In some examples, each logical component may just be the portion of the memory 120 or other physical memory that comprises instructions executable with the processor 106, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system 100 and its logic and data structures may be stored on, distributed across, or read from one or more types of computer readable storage media. Examples of the computer readable storage medium may include a hard disk, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks and flash memory drives. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor 106 or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor 106 may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

Advantageously, the multiwavelength ultrasound system 100 may be engaged non-invasively and may also be more quickly utilized compared to known methods for determining if a concentration of cells exceeds the predetermined threshold.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A multiwavelength ultrasound system configured to non-invasively aggregate and visualize biological cells in an aqueous media, the multiwavelength ultrasound system comprising:

a first ultrasound device configured to produce a first ultrasound wave having a frequency lower than 300 kHz, the first ultrasound wave configured to agglomerate the biological cells in the aqueous media via acoustic focusing;

a second ultrasound device configured to produce a second ultrasound wave having a frequency greater than 300 kHz, the second ultrasound wave configured to determine at least one of a location and a position of the agglomerated biological cells in the aqueous media;

a processor configured to:

selectively actuate at least one of the first ultrasound device and the second ultrasound device;

determine a density of the biological cells; and output a concentration of the biological cells;

wherein the processor determines for a creep velocity of each biological cell as a function of a position of each biological cell.

2. The multiwavelength ultrasound system of claim 1, wherein the first ultrasound wave has a frequency of 105 kHz.

3. The multiwavelength ultrasound system of claim 1, wherein the second ultrasound wave has a frequency greater than 1 MHz.

4. The multiwavelength ultrasound system of claim 1, wherein the first ultrasound wave aggregates the biological cells into substantially parallel lines.

5. The multiwavelength ultrasound system of claim 1, wherein the first ultrasound wave aggregates the biological cells into substantially arc-shaped lines.

6. The multiwavelength ultrasound system of claim 1, wherein the first ultrasound device is disposed substantially perpendicular to the second ultrasound device.

7. The multiwavelength ultrasound system of claim 1, wherein the processor detects a minimum threshold of the biological cells of three to thirty cells per cubic millimeter.

8. The multiwavelength ultrasound system of claim 1, wherein the processor determines if the concentration of the biological cells exceeds a predetermined threshold of ten to one-hundred cells per microliter.

9. A multiwavelength ultrasound system configured to non-invasively aggregate and visualize biological cells in an aqueous media, the multiwavelength ultrasound system comprising:

a first ultrasound device configured to produce a first ultrasound wave and a second ultrasound wave, the first ultrasound wave having a frequency lower than 300 kHz, the first ultrasound wave configured to agglomerate the biological cells in the aqueous media via acoustic focusing, the second ultrasound wave having a frequency greater than 300 kHz, the second ultrasound wave configured to determine at least one of a location and a position of the agglomerated biological cells in the aqueous media;

a processor configured to:

selectively actuate at least one of the first ultrasound device and the second ultrasound device;

determine a density of the biological cells; and output a concentration of the biological cells, wherein the processor determines for a creep velocity of each biological cell as a function of a position of each biological cell.

10. A method of using a multiwavelength ultrasound system configured to non-invasively aggregate and visualize biological cells, the method including the steps of:

providing a first ultrasound device, a second ultrasound device, and a processor, wherein the first ultrasound device is configured to produce a first ultrasound wave having a frequency lower than 300 kHz, the first ultrasound wave is configured to aggregate the biological cells, the second ultrasound device is configured to produce a second ultrasound wave having a frequency greater than 300 kHz, the second ultrasound wave is configured to determine at least one of a location and a position of the biological cells, wherein the processor determines for a creep velocity of each biological cell as a function of a position of each biological cell, the processor is configured to:

selectively actuate at least one of the first ultrasound device and the second ultrasound device, determine a density of the biological cells, and output a concentration of the biological cells;

generating the first ultrasound wave;

aggregating the biological cells;

generating the second ultrasound wave;

determining at least one of the location and the position of the biological cells;

determining the density of the biological cells; and outputting a concentration of the biological cells.

11. The method of claim 10, further comprising a step of varying the frequency of the first ultrasound wave.

12. The method of claim 10, further comprising a step of repositioning the first ultrasound device from a first position along a first axis to one of a second position along a second axis and a third position along a third axis, the first axis is spaced at a substantially equilateral angle between each of the second axis and the third axis.

13. The method of claim 12, wherein the processor autonomously repositions the first ultrasound device from the first position to one of the second position and the third position.

14. The method of claim 10, wherein the first ultrasound device includes a plurality of ultrasound devices evenly positioned around a circumference of the biological cells.

15. The method of claim 14, wherein each of the plurality of first ultrasound devices emits the first ultrasound wave simultaneously.

16. The method of claim 10, wherein the processor determines for the creep velocity of each biological cell as a function of position, x, utilizing a first algorithm:

$$v_{creep} = \frac{1}{5}\frac{\pi}{f\lambda}\left(P_{max}\frac{r^2}{\eta\lambda}\right)^2 (1 + \phi)^2 \sin(4\pi x/\lambda)$$

17. The method of claim 16, wherein the processor is further configured to integrate the creep velocity over time to determine a total displacement of a particle from starting position, x.

18. The method of claim 17, wherein the processor integrates the creep velocity over time to determine the total displacement of a particle from starting position, x, utilizing Euler's method, where F represents a derivative of y with respect to x, and h represents a fixed increment in x:

$$Y_n = Y_{n-1} + hF(X_{n-1}, Y_{n-1})$$

19. The method of claim 10, wherein the processor determines for the creep velocity of each biological cell as a function of position, x, utilizing a second algorithm:

$$\frac{v_{creep}}{c} = \frac{1}{5}\pi\left(\left(\frac{P_{max}}{f\eta}\right)\left(\frac{r}{\lambda}\right)^2\right)^2 (1 + \phi)^2 \sin\left(4\pi\left(\frac{x}{\lambda}\right)\right)$$

\* \* \* \* \*